United States Patent [19]
Wenzel et al.

[11] Patent Number: 5,968,792
[45] Date of Patent: Oct. 19, 1999

[54] CALCIUM ACTIVATION OF LIPASE ENZYME IN PROCESS OF PRESSURE SPLITTING GLYCERIDES

[75] Inventors: Jon Douglas Wenzel, Cincinnati; Kevin W. Anderson, Indian Springs, both of Ohio

[73] Assignee: Henkel Corporation, Gulph Mills, Pa.

[21] Appl. No.: 08/769,966

[22] Filed: Dec. 19, 1996

[51] Int. Cl.[6] .................................................. C12P 7/62
[52] U.S. Cl. ..................... 435/134; 435/198; 435/135
[58] Field of Search .................................. 435/134, 135, 435/198

[56] References Cited

U.S. PATENT DOCUMENTS 5,273,898  12/1993  Ishii ........................................ 435/198
5,677,160  10/1997  Oester ..................................... 435/198

OTHER PUBLICATIONS

Sonntag et al., J. Am. Oil Chem. Soc.(1979), 56, 729A–732A.

Fu et al., J. Am. Oil Chem. Soc. (1995), 72(5), 527–531.

Parijs et al., Acta Gastro–Enterol Belg 34 (1). 1971 79–85.

Aizono et al., Agric Biol Chem 37 (9). 1973 2031–2036.

Piazza et al., Biotechnol. Lett. (1989), 11(7), 487–492.

Van Loon, J.C., Chemical Analysis of Inorganic Constituents of Water, 1982, CRC Press, pp. 69–73.

*Primary Examiner*—Irene Marx
*Attorney, Agent, or Firm*—Ernest G. Szoke; Wayne C. Jaeschke; Steven J. Trzaska

[57] ABSTRACT

A process for pressure splitting glycerides into fatty acids and glycerols involving the steps of: (a) providing a glyceride feedstock; (b) providing a hydrolytic lipase enzyme; (c) providing an alkaline earth metal selected from the group consisting of calcium, magnesium, and mixtures thereof; (d) mixing components (a)–(c) in the presence of water and with agitation, at a temperature ranging from about 50 to about 60° C. to form a partially hydrolyzed glyceride feedstock; (e) introducing the partially hydrolyzed glyceride feedstock into a pressure splitter; and (f) splitting the partially hydrolyzed glyceride feedstock in the pressure splitter into carboxylic acids and glycerols.

15 Claims, No Drawings

CALCIUM ACTIVATION OF LIPASE ENZYME IN PROCESS OF PRESSURE SPLITTING GLYCERIDES

FIELD OF THE INVENTION

This invention relates to improvements in the presplitting of fats and oils by means of lipase hydrolysis utilizing calcium as an activator for lipase.

BACKGROUND OF THE INVENTION

Fatty acids are carboxylic acids having varying degrees of unsaturation and molecular weight. Fatty acids are used in a wide variety of products, such as in soaps and surfactants, lubricants, paints and coatings, candles, and in a variety of other agricultural, industrial, and personal care products. Glycerine, or 1,2,3-propanetriol, is used as a humectant, plasticizer, emollient, and lubricant in a wide variety of industrial and personal care applications.

Though fatty acids and glycerine have been produced synthetically, a substantial portion of these materials are obtained from naturally derived fats and oils. Fats and oils are also known as triglycerides, which are the reaction products of an alcohol, glycerine, and an acid, the fatty acids discussed above. To produce fatty acids and glycerine from fats and oils, the fat or oil is hydrolyzed or "split", typically by the action of heat and pressure in the presence of water, to break the bonds between the acid and the alcohol.

Typically, the fat or oil is split commercially in a pressure splitter wherein preferably the fat or oil is introduced at one end and water introduced at the opposite end thereof in a countercurrent flow pattern. In operation, the pressure splitter provides substantial amounts of heat and pressure to the mixture of triglyceride and water to effect the hydrolysis. However, because the triglyceride is hydrophobic, the amount of actual contact between the water phase and the fat phase is relatively low. It is believed that after a period of time in the splitter individual triglyceride molecules incompletely hydrolyze, splitting off one acid molecule to create a di-glyceride or two acid molecules to form a monoglyceride. The mono- and di-glycerides are less hydrophobic than the starting triglyceride, and mix more thoroughly with water. As a result, the mono- and di-glycerides function as emulsifiers to improve mixing of the triglyceride with water. Under the turbulent conditions within the pressure splitter, it is believed that the mono- and di-glycerides improve the extent of mixing between the triglyceride and water, thereby facilitating the hydrolysis reaction.

The period of time during which the hydrolysis rate is depressed is known as the induction period. During the induction period, heat is inputted to the pressure splitter and pressure is generated, but few hydrolysis products are being produced. The volume of triglycerides hydrolyzed within the pressure splitter would be increased substantially if the induction period could be eliminated or at least substantially reduced.

Several methods have been used in the past to decrease the induction time in the pressure splitter. Surfactants have been added to the triglyceride feed to aid mixing between the water and fat layers in what became known as the Twitchell process. These surfactants were typically organo-sulphonic acids. However, after the splitting operation the surfactants had to be removed from the system, typically by extraction, which was time consuming and difficult to accomplish. Also, catalysts have been used to increase the rate of hydrolysis of the triglyceride and thereby the amount of mono- and di-glycerides. However, after the splitting operation was completed, the catalysts had to be removed from the system to eliminate undesirable contamination effects. It was also known that starting the pressure splitting operation with a fat or oil having a relatively high acid value would result in a decreased induction period in the splitting process. This could be accomplished by back-adding a blend of free acids, mono- and di-glycerides to the fat or oil feedstock. However, this step would not increase the overall efficiency of the pressure splitting process because a portion of the raw feedstock had to be replaced with the partially hydrolyzed portion. In effect, a portion of the feedstock had to be recycled through the splitter instead of subjecting the feedstock to splitting only once. In yet another method for decreasing the induction period, the feedstock in a storage tank prior to pressure splitting could be subjected to high temperatures in the presence of water to force the hydrolysis reaction to begin. However, the subjection of the feedstock to such high temperatures, in a range above about 80° C., would cause formation of undesirable oxidation products and color bodies which would degrade the quality of the feedstock.

SUMMARY OF THE INVENTION

The present invention relates to a process for partially hydrolyzing glycerides into fatty acids and glycerols involving the steps of:

(a) providing a glyceride feedstock;

(b) providing a hydrolytic lipase enzyme;

(c) providing an alkaline earth metal selected from the group consisting of calcium, magnesium, and mixtures thereof; and (d) mixing components (a)–(c), in the presence of water and with agitation, at a temperature ranging from about 50 to about 60° C. to form the partially hydrolyzed glyceride feedstock.

The present invention also provides a process for pressure splitting glycerides into fatty acids and glycerols involving the steps of:

(a) providing a glyceride feedstock;

(b) providing a hydrolytic lipase enzyme;

(c) providing an alkaline earth metal selected from the group consisting of calcium, magnesium, and mixtures thereof;

(d) mixing components (a)–(c), in the presence of water and with agitation, at a temperature ranging from about 50 to about 60° C. to form the partially hydrolyzed glyceride feedstock;

(e) introducing the partially hydrolyzed glyceride feedstock into a pressure splitter; and (f) splitting the partially hydrolyzed glyceride feedstock in the pressure splitter into carboxylic acids and glycerols.

DESCRIPTION OF THE INVENTION

Other than in the operating examples, or where otherwise indicated, all numbers expressing quantities of ingredients or reaction conditions are understood as being modified in all instances by the term "about".

The glyceride feedstock which may be employed in the present invention is typically obtained from naturally derived fats and oils examples of which include tallow, lard, coconut oil, canola oil, palm oil, and mixtures thereof. The partial hydrolyzing/splitting step is preferably performed in a batch process during that time while the glyceride feedstock is stored in a holding tank prior to pressure splitting. The fat or oil is typically contained in a storage tank which is heated to a temperature of from about 50 to about 60° C. for a period of at least 2 days prior to pressure splitting, and partial hydrolysis can be performed during that period of time.

The hydrolytic lipase enzymes which may be employed in the process of the invention are those which are commercially available for use in hydrolyzing fats into fatty acids and glycerols. A particularly preferred lipase is one that functions well at the water-oil interface and specifically hydrolyzes fatty acids from the C-1 and C-3 positions of the triglyceride, commercially available from Novo Industries, under the tradename LIPOLASE® 100T.

The alkaline earth metals which may be employed in the present are selected from the group consisting of calcium, magnesium and mixtures thereof. Since calcium does not occur free in nature, it must be derived from chemical processes. It is most often derived from either the electrolysis of fused calcium chloride or by a thermal process under high vacuum from lime reduced with aluminum. The calcium used in the process of the invention can be obtained from any known source such as, for example, commercially available calcium carbonate may be obtained commercially for use in the present invention.

Another highly suitable source of calcium can be found in a by-product stream generated during oleochemical processing. The by-product stream consists of the material removed from a fat storage tank during the dewatering operation just prior to the pressure splitting of the fat. This by-product stream separates into three distinct phases: 1) a top phase consisting primarily of fat, 2) a middle emulsion phase consisting of fat and water, enriched in calcium and containing calcium fatty acid soaps, and 3) a bottom phase consisting of water and sludge. It is the middle phase enriched in calcium and containing the calcium soaps of the fatty acids that has been found to greatly improve presplitting hydrolysis performance when added to the fat prior to enzyme loading.

Magnesium, on the other hand, occurs widespread in nature in the ores dolomite, magnesite, and carnallite, and as the chloride in seawater, underground natural brines, and salt deposits. Metallic magnesium is produced by the electrolysis of molten magnesium chloride or thermal reduction of the oxide.

The water needed to effectuate the hydrolysis of the glyceride feedstock may be introduced into the process from any known source, either as an individual component or in admixture with either the lipase and/or calcium components.

In one preferred embodiment of the present invention, a glyceride feedstock present in a storage container is heated to a temperature of from about 50 to about 60° C. Calcium is then added to the heated glyceride feedstock in an amount ranging from about 10 to about 500 ppm, and preferably about 250 ppm, per gram of glyceride feedstock, wherein the calcium acts as an activator for the lipase enzyme. It has been observed that glyceride feedstocks containing low levels of calcium, i.e., less than 5–10 ppm, per gram of glyceride feedstock, exhibit poor enzymatic hydrolysis performance, thus contributing to the lag in induction time for hydrolysis. This phenomenon frequently occurs in fats that are of higher quality or fats that have been previously exposed to processes which have a tendency to remove calcium such as, for example, the acid washing of fats or oils.

The lipase enzyme is then added to the mixture of heated glyceride feedstock and calcium, with agitation, and preferably in the form of an aqueous slurry. The glyceride/lipase/calcium solution is preferably agitated at a rate sufficient to render the lipase miscible or finely dispersed in the feedstock. The agitation is continued for a period of time sufficient to raise the acid value, and at a temperature optimally just below the deactivation temperature of the lipase. It has been found that agitation of a tallow feedstock with lipase and water for about 24 to 48 hours at temperatures of up to about 60° C. can produce acid values in the range of from about 30 to about 60 (mg KOH/g sample). A particularly preferred acid value for the partially hydrolyzed glyceride feedstock is from about 40 to about 60. In comparison, complete hydrolysis of tallow would produce an acid value from the liberated carboxylic acids of about 200.

The lipase is combined with the fat or oil feedstock in a preferred range of from about 40 ppm to about 100 ppm of lipase per gram of glyceride feedstock. Levels of lipase outside this range may be used, as well as different lipase enzymes, so long as the amount and type is effective in producing a partial split acid value, preferably of at least about 50. The upper acid value limit is dictated by the nature of the lipase reaction, which is discussed in more detail hereinbelow. The lipase is preferably mixed with water prior to blending with the feedstock. It has been found that water may become a limiting reagent at concentrations of 0.01 milliliters per gram weight of glyceride feedstock or less. Good results were obtained when the resultant aqueous phase comprises from about 0.025 to about 0.035, and preferably about 0.03 milliliters of water per gram weight of the fat or oil feedstock.

The operation of commercial pressure splitters is well known in the industry. Essentially, a glyceride in the form of an oil, molten fat, or a blend thereof is introduced into a reactor with water, and heat is applied. As the temperature increases, so does the pressure. In batch splitters, the components are mixed by agitation. In continuous splitters, the triglyceride is typically introduced from the bottom, water from the top, and the difference in densities and the input pumping force causes mixing. Temperatures in the continuous pressure splitters range from about 200 to about 300° C., preferably about 250 to about 280° C., and the pressure within the reactor ranges preferably from about 550 to about 950 psi. The triglyceride is mixed in the continuous splitter with water, which comprises about 40 to about 50% by weight of the reactor contents. On a laboratory scale, the pressure splitting was conducted as a batch process. Batch pressure splitting involves temperatures in the range of about 240 to about 260° C., and pressures preferably in the range of about 450 to about 700 psi. Water content in the batch process is slightly higher, in the range of about 50 to about 70% by weight of the reactor contents.

To obtain maximum efficiency from the pressure splitter, then, it is desired that the acid value of a triglyceride feedstock entering the splitter be at least about 40, and preferably from about 40 to about 60. To achieve this acid value with corresponding production of mono- and diglycerides, the presplitting process utilizing lipase and calcium is employed.

For a batch process, the partial splitting of triglyceride utilizing lipase is conducted at a temperature below the deactivation temperature of the lipase in a storage vessel with air atmosphere such as a holding tank in the presence of water and with agitation. Agitation is important to maximize the interfacial surface area between the water phase and the hydrophobic triglyceride and calcium. Satisfactory results were obtained by agitating the triglyceride, calcium and lipase solution at a rate sufficient to maintain miscibility of the phases.

It is believed that the process of partial splitting combined with pressure splitting will be applicable to effecting hydrolysis of any glyceride molecule having an ester linkage.

In accordance with the surprising discovery of the present invention, it should also be noted that alkaline earth metals such as those disclosed above, and most preferably calcium, may also be used to activate lipases in not only ester hydrolysis processes, but also the following processes: ester synthesis (acid+alcohol), and interesterification, including acidolysis (ester+acid), alcoholysis (ester+alcohol), and ester interchange (ester +ester), or transesterification. By using calcium as an activator for lipase enzymes, esters may be synthesized and/or interesterified in a more efficient manner, resulting in the increased production of the desired final product.

The present invention will be better understood from the examples which follow, all of which are intended to be illustrative only and not meant to unduly limit the scope of the invention. Unless otherwise indicated, percentages are on a weight-by-weight basis.

EXAMPLE 1

10 grams of Choice White Grease (pork fat) is added to a 20 ml vial and maintained at a temperature of 50° C. 0.3 ml of tap water containing 0.00075 gram of NOVO LIPOLASE® 100T and 0.0001 gram CaCO₃ is added to the fat, and the contents of the vial are continuously mixed using a stir bar.

EXAMPLE 2

10 grams of DM tallow fat and 0.2 grams of Class 3, i.e., a mixture of calcium and fatty acid soap, are added to a 20 ml vial and maintained at a temperature of 50° C. 0.3 ml of water containing 0.00044 gram of NOVO LIPOLASE® 100T is added to the fat, and the contents of the vial are continuously mixed using a stir bar.

COMPARATIVE EXAMPLE 1

10 grams of Choice White Grease (pork fat) is added to a 20 ml vial and maintained at a temperature of 50° C. 0.3 ml of tap water containing 0.00075 grams of NOVO LIPOLASE® 100T is added to the fat, and the contents of the vial are continuously mixed using a stir bar.

COMPARATIVE EXAMPLE 2

10 grams of DM tallow is added to a 20 ml vial and maintained at a temperature of 50° C. 0.3 ml of water containing 0.00044 gram of NOVO LIPOLASE® 100T is added to the fat, and the contents of the vial are continuously mixed using a stir bar.

The amount of fatty acid liberated from the fat source was determined by measuring the acid value of the fat prior to the addition of the above-disclosed components, and at certain intervals thereafter. The higher the acid value after the additions, the greater the amount of fatty acid liberated (split) from the fat source. The results thereof are found in Table 1 below.

TABLE 1

| | Initial Acid Value | Acid Value after approx. 16 hrs. | Acid Value after approx. 40 hrs. |
| --- | --- | --- | --- |
| Example 1 | 6.8 | 30.7 | 47.0 |
| Example 2 | 12.1 | 33.1 | 48.8 |
| Comp. Example 1 | 6.8 | 21.3 | 29.2 |
| Comp. Example 2 | 12.1 | 12.0 | 12.1 |

As can be seen from the results, by employing calcium in combination with a lipase enzyme, the amount of fatty acid liberated from the fat source is significantly increased.

What is claimed is:

1. A process for pressure splitting glycerides into fatty acids and glycerols involving the steps of:
   (a) providing a glyceride feedstock;
   (b) providing from about 40 to about 100 ppm, based on the weight of the glyceride feedstock, of a hydrolytic lipase enzyme;
   (c) providing from about 10 to about 500 ppm, based on the weight of the glyceride feedstock, of calcium;
   (d) mixing components (a)–(c) in the presence of water and with agitation, at a temperature ranging from about 50 to about 60° C. to form a partially hydrolyzed glyceride feedstock;
   (e) introducing the partially hydrolyzed glyceride feedstock into a pressure splitter; and
   (f) splitting the partially hydrolyzed glyceride feedstock in the pressure splitter into carboxylic acids and glycerols.

2. The process of claim 1 wherein the partially hydrolyzed glyceride feedstock has an acid value ranging from about 40 to about 60.

3. The process of claim 1 wherein the pressure splitter is heated to a temperature ranging from about 250 to about 280° C.

4. The process of claim 1 wherein the pressure splitter is pressurized to a pressure ranging from about 550 to about 950 psi.

5. The process of claim 1 wherein the water in step (d) is present in an amount greater than 0.01 ml per gram of glyceride feedstock.

6. The process of claim 1 wherein the glyceride feedstock is selected from the group consisting of tallow, lard, coconut oil, canola oil, palm oil, and mixtures thereof.

7. The process of claim 5 wherein the water in step (d) is present in an amount of from about 0.025 ml to about 0.035 ml per gram of glyceride feedstock.

8. The process of claim 1 wherein the calcium is present in the form of calcium soap.

9. The process of claim 1 wherein the calcium is present in the form of calcium carbonate.

10. A process for partially hydrolyzing glycerides into fatty acids and glycerols involving the steps of:
   (a) providing a glyceride feedstock;
   (b) providing from about 40 to about 100 ppm of a hydrolytic lipase enzyme, per gram of glyceride feedstock;
   (c) providing from about 10 to 500 ppm of calcium, per gram of glyceride feedstock; and (d) mixing components (a)–(c), in the presence of water and with agitation, at a temperature ranging from about 50 to about 60° C. to form the partially hydrolyzed glyceride feedstock.

11. The process of claim 10 wherein the water in step (d) is present in an amount greater than 0.01 ml per gram of glyceride feedstock.

12. The process of claim 10 wherein the glyceride feedstock is selected from the group consisting of tallow, lard, coconut oil, canola oil, palm oil, and mixtures thereof.

13. The process of claim 11 wherein the water in step (d) is present in an amount ranging from about 0.025 ml to about 0.035 ml per gram of glyceride feedstock.

14. The process of claim 10 wherein the calcium is present in the form of calcium soap.

15. The process of claim 10 wherein the calcium is present in the form of calcium carbonate.

* * * * *